US00PP37423P2

(12) United States Plant Patent
Kordes et al.

(10) Patent No.: US PP37,423 P2
(45) Date of Patent: May 12, 2026

(54) MINIATURE ROSE PLANT NAMED 'KORpot140'

(50) Latin Name: *Rosa hybrida*
Varietal Denomination: KORpot140

(71) Applicant: W. KORDES' SÖHNE Rosenschulen GmbH & Co KG, Klein Offenseth-Sparrieshoop (DE)

(72) Inventors: Wilhelm-Alexander Kordes, Klein Offenseth-Sparrieshoop (DE); Britta Feuerhahn, Klein Offenseth-Sparrieshoop (DE)

(73) Assignee: W. KORDES' SÖHNE Rosenschulen GmbH & Co KG, Klein Offenseth-Sparrieshoop (DE)

( * ) Notice: Subject to any disclaimer, the term of this patent is extended or adjusted under 35 U.S.C. 154(b) by 0 days.

(21) Appl. No.: 19/375,461

(22) Filed: Oct. 31, 2025

(51) Int. Cl.
*A01H 5/02* (2018.01)
*A01H 6/74* (2018.01)

(52) U.S. Cl.
USPC ..... Plt./122

(58) Field of Classification Search
USPC ..... Plt./122, 150, 129
CPC . A01H 5/02; A01H 5/00; A01H 6/749; A01H 6/74
See application file for complete search history.

(56) References Cited

U.S. PATENT DOCUMENTS

PP18,840 P2 5/2008 Kordes
PP23,795 P2 * 8/2013 Kordes ..... A01H 5/02 Plt./122

* cited by examiner

*Primary Examiner* — June Hwu
(74) *Attorney, Agent, or Firm* — Panitch Schwarze Belisario & Nadel LLP; Stephany G. Small; Travis W. Bliss

(57) ABSTRACT

A new and distinct variety of miniature rose plant, referred to by its cultivar name, 'KORpot140', is described. The new plant variety forms in abundance on a substantially continuous basis red-colored blossoms. The growth habit is compact. Glossy, medium green foliage is formed. Additionally, the new plant variety is particularly well suited for growing as distinctive ornamentation in the landscape.

1 Drawing Sheet

Latin name of genus and species of plant claimed: *Rosa hybrida.*

Variety denomination: 'KORpot140'.

STATEMENT REGARDING PRIOR DISCLOSURES BY THE INVENTOR

The first sale or offer for sale of the new plant variety was November 2024 on the ROSA DANICA website. The first sale or offer for sale of the new plant variety was by a joint inventor or another who obtained the new plant variety directly or indirectly from a joint inventor. No plants of the new variety have been sold in this country or anywhere in the world, nor has any disclosure of the new plant been made, more than one year prior the effective filing date of this application, and such sale or disclosure within one year was either derived directly or indirectly from a joint inventor.

BACKGROUND OF THE INVENTION

The new variety of miniature rose plant of the present invention was created by controlled breeding in 2020 in Offenseth-Sparrieshoop, Germany by artificial pollination wherein two parents were crossed which previously had been studied in the hope that they would contribute the desired characteristics. The female parent (i.e., the seed parent) of the new variety was an unnamed seedling (not patented) that was a product of the cross between an unnamed seedling and 'KORelamur' (not patented). The male parent (i.e., the pollen parent) of the new variety was a different unnamed seedling (not patented) that was a product of the cross between 'RUIe057a' (not patented) and 'KORpolare' (U.S. Plant Pat. No. 18,840).

The parentage of the new variety can be summarized as follows:

(unnamed seedling x 'KORelamur') x ('RUIe057a' x 'KORpolare')

The seeds resulting from the above pollination were sown and small plants were obtained which were physically and biologically different from each other. Selective study resulted in the identification of a single plant of the new variety.

The new plant variety has been found to undergo asexual propagation at Klein Offenseth-Sparrieshoop, Germany by a number of routes such as vegetative cuttings. Asexual propagation techniques in Klein Offenseth-Sparrieshoop, Germany, such as vegetative cuttings, have shown that the characteristics of the new plant variety are homogeneous, stable, and strictly transmissible by such asexual propagation from one generation to another. Accordingly, the new plant variety undergoes asexual propagation in a true-to-type manner.

SUMMARY OF THE INVENTION

It was found that the new variety of miniature rose plant of the present invention possesses the following combination of characteristics:

(a) abundantly and substantially continuously forming red-colored blossoms,
(b) exhibiting a compact growth habit, and
(c) forming glossy, medium green foliage.

The new plant variety well meets the needs of the horticultural industry. It can be grown to advantage as distinctive ornamentation in parks, gardens, public areas, and residential landscapes. Accordingly, it is particularly well suited for growing in the landscape.

The new plant variety can be readily distinguished from its ancestors. More specifically, the new plant variety displays a more coral red flower color, produces between 1 and 3 blooms per stem, and exhibits a larger flower size compared to the unnamed seedling parent (i.e., the seed parent) which displays dark red colored flowers and produces blooms in clusters. Additionally, the new plant variety displays a more coral red colored blossom and a more compact growth habit compared to the different unnamed seedling parent (i.e., the pollen parent), which displays pinkish red colored flowers. Moreover, the new plant variety can be readily distinguished from non-parental related similar varieties. For example, the new plant variety displays smaller-sized foliage and a more coral red flower color, whereas the 'KORpot003' variety (U.S. Plant Pat. No. 23,795) displays dark red colored blossoms.

The new plant variety has been named the 'KORpot140' variety.

BRIEF DESCRIPTION OF THE PHOTOGRAPH

The accompanying photograph shows, as nearly true as it is reasonably possible to make the same in a color illustration of this character, a typical specimen of the new plant variety and blossoms of the new plant variety. The illustrated rose plant of the new variety was approximately sixteen weeks of age and was grown indoors on its own roots in a 10.5 cm container in Odense, Denmark.

Drawing—illustrates a specimen of the plant displaying flowers at varying points of opening.

DETAILED BOTANICAL DESCRIPTION

The chart used in the identification of colors is that of The Royal Horticultural Society (The R.H.S. Colour Chart, 2015 edition). The terminology which precedes reference to the chart has been added to indicate the corresponding color in more common terms. The R.H.S. Colour Chart designations used herein represent the closest color observed on the majority of the specified botanical features. The description is based on a three-year-old specimen of the new variety, observed during August 2025, while growing on its own roots in a two-gallon container in a greenhouse in Cochranville, Pennsylvania.

Botanical classification: *Rosa hybrida* cultivar 'KORpot140'.

*Commercial classification*: Miniature Rose.

Plant:

*Habit*.—Compact.

*Height*.—Approximately 34.0 cm on average from the top of the soil plane.

*Width*.—Approximately 30.0 cm on average.

Branches:

*Stem color*.—Old wood: Green Group 143A. — young stems: Green Group 143C.

*Length*.—Main stems: approximately 34.0 cm on average. — secondary stems: approximately 24.0 cm on average.

*Diameter*.—Main stems: approximately 5.0 mm on average. — secondary stems: approximately 3.0 mm on average.

*Texture*.—Smooth.

*Prickles*.—Amount: substantial; 6 to 10 prickles per internode with many additional small, hispid-like prickles intermixed. — young prickles: length is approximately 3.0 mm on average; width is approximately 3.0 mm on average at point of attachment; and color is Yellow-Green Group 148C. — old prickles: length is approximately 3.0 mm on average; width is approximately 3.0 mm on average at point of attachment; and color is Greyed-Orange Group 165B.

Leaflets:

*Number*.—5 and 7.

*Shape*.—Ovate; apex is acute to acuminate; and base is cuneate.

*Arrangement*.—Odd-pinnate.

*Margin*.—Serrate.

*Undulation*.—Moderate.

*Glossiness of upper side*.—Glossy.

*Texture*.—Upper surface: smooth. — under surface: smooth.

*Venation pattern*.—Reticulate.

*Size*.—Terminal leaflet: length is approximately 4.0 cm on average; width is approximately 2.0 cm on average. — lower leaflets: length is typically 2.0 cm to 3.5 cm; width is typically 1.5 cm to 2.0 cm. — 5-Leaflet leaf: length is approximately 8.5 cm on average; width is approximately 7.0 cm on average.

Foliage:

*Young foliage*.—Upper surface color: Green Group 139B with indistinguishable venation. — under surface color: Green Group N138C with indistinguishable venation.

*Old foliage*.—Upper surface color: Green Group 137A with indistinguishable venation. — under surface color: Green Group 138B with indistinguishable venation.

*Petiole*.—Texture: upper surface is hispidulous; under surface is smooth, with one or two prickles between first set of lower leaves and stipules. — length: approximately 2.0 cm on average. — width: approximately 1.0 mm on average. — upper surface color: Green Group 143A. — under surface color: Green Group 143A.

*Rachis*.—Length: approximately 2.3 cm on average. — width: approximately 1.0 mm on average. — upper surface color: Green Group 143B. — under surface color: Green Group 143A.

*Stipules*.—Length: approximately 2.0 cm on average. — width: approximately 7.0 mm on average. — margin: entire to erose. — upper surface color: Green Group 143A. — lower surface color: Yellow-Green Group 144A.

Inflorescence:

*Number of flowers*.—About 25 to 30 blooms on average on a plant at once.

*Number of blossoms per stem or in a cluster*.—Typically between 1 and 3 blooms per stem on average.

*Peduncle*.—Color: Yellow-Green Group 144A. — diameter: approximately 4.0 mm on average. — length: approximately 4.5 cm on average. — surface texture: hispid, with substantial prickles in addition to the hispid protrusions.

*Sepals*.—Number: 5. — upper surface color and texture: Yellow-Green Group 151A, puberulent and slightly hispid. — under surface color and texture: Yellow-Green Group N144A, with small amount of Greyed-Red Group 180A streaking, covered in short pubescence. — size: length is approximately 2.6 cm on average; width is approximately 9.0 mm on average. — margin: entire with extensions on most sepals measuring approximately 3.0 mm in length and 1.0 mm in width on average. — shape: lanceolate. — apex: acute to aristate. — base: truncate as it joins the receptacle.

*Buds*.—Shape: ovoid. — size: length is approximately 1.5 cm on average; width is approximately 1.0 cm on average. — color (when opening): Orange-Red Group N34A.

*Flower*.—Form: Double, cuplike. — profile: concave as it opens, and then outer petals are convex as the bloom ages and opens further. — diameter: approximately 6.5 cm on average. — height: approximately 1.8 cm on average. — duration: on the plant approximately 10 to 15 days. — petal color when first and fully opened: upper surface is Red Group 46A, slightly lightening to Red Group N45D at base with no visible basal spot; under surface is Red Group 51A with no visible basal spot. — petal color at end of bloom: upper surface is Red Group 53B with no visible basal spot; under surface is Red Group 51A with no visible basal spot. — petals reflex one by one: yes.

*Fragrance*.—Very slight to no noticeable scent.

*Petal*.—Number: 20 to 25 on average. — drop: good. — length: approximately 2.6 cm on average. — width: approximately 2.5 cm on average. — overall shape: broadly obovate. — margin: entire with moderate undulation. — apex shape: rounded to slightly reniform. — base shape: cuneate. — texture: upper surface is smooth; under surface is smooth.

*Petaloids*.—Number: approximately 4 on average. — length: approximately 1.4 cm on average. — width: approximately 3.0 mm on average. — color: upper surface is Red Group 46A with no visible basal spot; under surface is Red Group 46A with no visible basal spot. — texture: upper surface is smooth; under surface is smooth. — margin: entire with moderate undulation. — shape: obovate. — apex: obovate. — base: linear.

*Stamen*.—Number: approximately 100. — anthers: number is approximately 100; color is Greyed-Orange Group 166A; length is approximately 1.0 mm on average; and shape is oval. — filaments: length is approximately 6.0 mm on average and color is Yellow Group 8A.

*Pistils*.—Arrangement: separate, but slightly fused. — number: approximately 90. — style: length is approximately 7.0 mm on average and color is Red Group 45A. — stigma: diameter is approximately 1.0 mm on average; shape is fan shaped; color is Yellow-Orange Group 17A.

*Receptacle*.—Diameter: approximately 8.0 mm on average. — depth: approximately 7.0 mm on average. — shape: urn shaped. — color: Yellow-Green Group 144B. — surface texture: covered in substantial thorns and small prickles.

*Pollen*.—Amount: none observed.

*Hips/seed*.—None observed.

Development:

*Vegetation*.—Glossy, medium green.

*Blossoming*.—Abundant and continuous from spring through frost; typically, in bloom outdoors from May to November in Southeastern Pennsylvania.

*Resistance to diseases*.—Good resistance to powdery mildew (*Podosphaera pannosa*).

*Hardiness*.—Unknown.

The new 'KORpot140' variety has not been observed under all possible environmental conditions to date. Accordingly, it is possible that the phenotypic expression may vary somewhat with changes in light intensity and duration, cultural practices, and other environmental conditions.

We claim:

1. A new and distinct variety of miniature rose plant named 'KORpot140' characterized by the following combination of characteristics:

(a) abundantly and substantially continuously forming red-colored blossoms, (b) exhibiting a compact growth habit, and (c) forming glossy, medium green foliage;

substantially as herein shown and described.

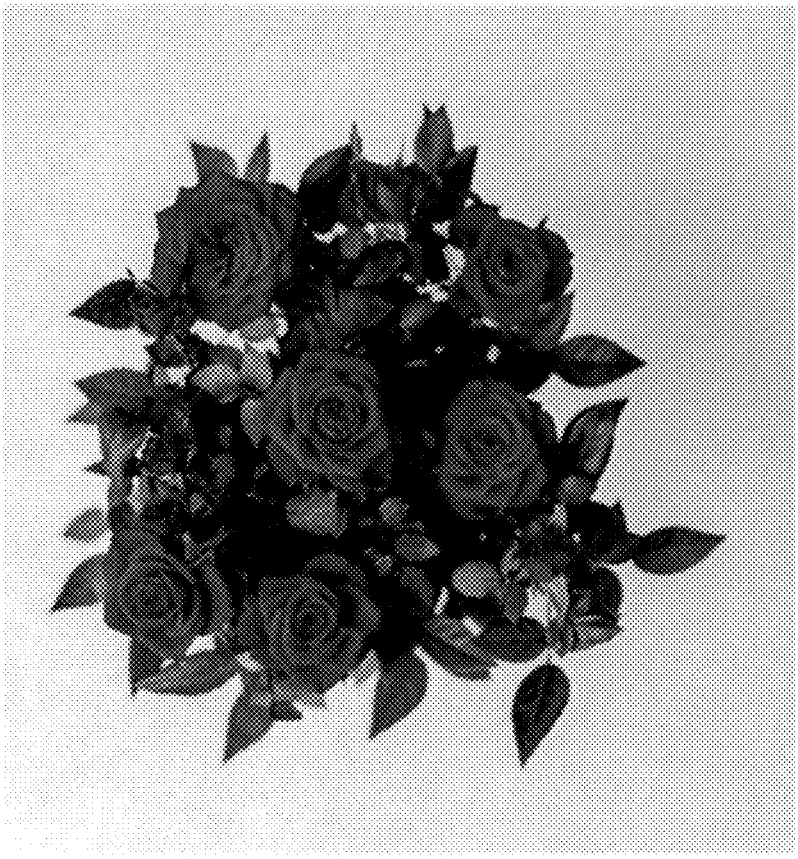

* * * * *